(12) United States Patent
Shi et al.

(10) Patent No.: US 11,757,132 B2
(45) Date of Patent: Sep. 12, 2023

(54) NON-AQUEOUS ELECTROLYTE FOR LITHIUM-ION BATTERY AND LITHIUM-ION BATTERY

(71) Applicant: SHENZHEN CAPCHEM TECHNOLOGY CO., LTD., Guangdong (CN)

(72) Inventors: Qiao Shi, Guangdong (CN); Muchong Lin, Guangdong (CN); Shiguang Hu, Guangdong (CN); Xionggui Lin, Guangdong (CN); Jiaojiao Yun, Guangdong (CN); Chang'an Zeng, Guangdong (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/735,109

(22) Filed: May 2, 2022

(65) Prior Publication Data
US 2022/0263133 A1  Aug. 18, 2022

Related U.S. Application Data

(62) Division of application No. 16/316,621, filed as application No. PCT/CN2016/113649 on Dec. 30, 2016, now Pat. No. 11,362,370.

(30) Foreign Application Priority Data

| Nov. 25, 2016 | (CN) | 201611054855.8 |
| Nov. 25, 2016 | (CN) | 201611055698.2 |
| Nov. 25, 2016 | (CN) | 201611063485.4 |

(51) Int. Cl.
| H01M 10/0567 | (2010.01) |
| H01M 10/0525 | (2010.01) |
| H01M 10/0569 | (2010.01) |
| H01M 10/056 | (2010.01) |
| C07D 327/10 | (2006.01) |
| C07D 317/10 | (2006.01) |
| C07F 9/06 | (2006.01) |
| C07F 9/113 | (2006.01) |

(52) U.S. Cl.
CPC ...... H01M 10/0567 (2013.01); C07D 317/10 (2013.01); C07D 327/10 (2013.01); C07F 9/062 (2013.01); C07F 9/113 (2013.01); H01M 10/056 (2013.01); H01M 10/0525 (2013.01); H01M 10/0569 (2013.01); H01M 2300/0037 (2013.01)

(58) Field of Classification Search
CPC ...... H01M 10/0567; H01M 10/0525; H01M 10/056; H01M 10/0569; H01M 2300/0037; H01M 2300/0034; C07D 317/10; C07D 327/10; C07F 9/062; C07F 9/113; Y02E 60/10
See application file for complete search history.

(56) References Cited

U.S. PATENT DOCUMENTS

| 2003/0113635 A1* | 6/2003 | Gan | H01M 4/587 |
| | | | 429/232 |
| 2008/0206649 A1* | 8/2008 | Kawashima | H01M 10/0567 |
| | | | 429/324 |
| 2008/0292971 A1* | 11/2008 | Ihara | H01M 10/052 |
| | | | 429/327 |
| 2011/0291042 A1* | 12/2011 | Li | H01M 4/525 |
| | | | 252/182.1 |
| 2016/0301104 A1* | 10/2016 | Shi | H01M 4/505 |

* cited by examiner

*Primary Examiner* — Muhammad S Siddiquee (57) ABSTRACT

A non-aqueous electrolyte for a lithium-ion battery and a lithium-ion battery. The non-aqueous electrolyte includes an unsaturated phosphate compound and a cyclic unsaturated carboxylic anhydride compound. The unsaturated phosphate compound has a structure represented by structural formula (4). $R_{13}$, $R_{11}$ and $R_{12}$ are each independently selected from a hydrocarbon group having 1 to 5 carbon atoms, and at least one of $R_{13}$, $R_{11}$ and $R_{12}$ is an unsaturated hydrocarbon group having a double bond or a triple bond. The unsaturated cyclic carboxylic anhydride compound having a structure represented by Structural Formula 5. $R_{14}$ is selected from the group consisting of an alkenylene group having 2 to 4 carbon atoms or a fluorinated alkenylene group having 2 to 4 carbon atoms. By means of the synergistic effect of two compounds, the non-aqueous electrolyte has excellent high-temperature cycling performance and storage performance, and also has lower impedance and good low-temperature performance.

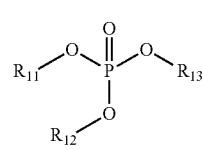

(4)

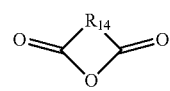

(5)

19 Claims, 1 Drawing Sheet

NON-AQUEOUS ELECTROLYTE FOR LITHIUM-ION BATTERY AND LITHIUM-ION BATTERY

TECHNICAL FIELD

The present application relates to the field of lithium-ion battery electrolyte, and more particularly to a non-aqueous electrolyte for lithium-ion battery and a lithium-ion battery.

BACKGROUND OF THE INVENTION

Lithium-ion batteries have the characteristics of high specific energy, high specific power and long cycling life. They are presently mainly used in the fields of 3 C digital consumer electronics, new energy power vehicles, and energy storage. With the continuously increased requirements for the mileage of new energy vehicles and the miniaturization of digital consumer electronics products, high energy density has become the main development trend of lithium-ion batteries. Increasing the operating voltage of lithium-ion batteries is an effective way to increase the energy density of the batteries.

Increasing the operating voltage of a lithium-ion battery tends to result in performance degradation. Because at high voltages, on the one hand, there is a certain instability in the crystal structure of the cathode of the battery, and structural collapse may occur in the process of charging and discharging, resulting in performance degradation; and on the other hand, at high voltages, the surface of the cathode is in a highly oxidative state and has a high activity, such that it will easily catalyze the oxidative decomposition of the electrolyte. The decomposition products of the electrolyte will easily deposit on the surface of the cathode, blocking the deintercalation channels for lithium ions, thereby degrading battery performances.

The electrolyte is a key factor affecting the overall performances of the battery. In particular, the additives in the electrolyte are particularly important for the performances of the battery. Therefore, in order to give full play to the performances of the power battery of the nickel-cobalt-manganese ternary material, the matching of the electrolyte holds the key. The currently practical electrolytes for lithium-ion batteries are the non-aqueous electrolytes added with a conventional film-forming additive such as vinylene carbonate (abbreviated as VC) or fluoroethylene carbonate (abbreviated as FEC). The addition of VC and FEC ensures the excellent cycling performances of the batteries. However, VC has poor stability at high voltages, and FEC tends to decompose and produce gas at high temperatures. Therefore, under high-voltage and high-temperature conditions, these additives are difficult to meet the performance requirements of lithium-ion batteries cycling at high voltages and high temperatures.

Patent application No. 201410534841.0 discloses a triple bond-containing phosphate compound as a novel film-forming additive, which not only improves the high-temperature cycling performance, but also significantly improves the storage performance. However, researchers in the art have found during researches that the triple bond-containing phosphate additive not only forms a film on the cathode, but also forms a film on anode. The film formation on the anode will significantly increase the impedance of the anode and significantly degrade the low-temperature performance.

Cyclic unsaturated carboxylic anhydride compounds as a lithium battery electrolyte additive have also long been reported in some related papers and patents. Having similar functional characteristics to the triple bond-containing phosphates, the cyclic unsaturated carboxylic anhydrides also significantly improve the high-temperature performance, but at the same time, they will also increase the battery impedance, and degrade the low-temperature performance, restricting the application of the lithium-ion batteries with non-aqueous electrolyte under low temperature conditions.

SUMMARY OF THE INVENTION

An object of the present application is to provide a non-aqueous electrolyte for lithium-ion battery, as well as a lithium-ion battery using the non-aqueous electrolyte.

In order to achieve the above object, the present application adopts the following technical solutions:

Technical Solution I:

In one aspect, the present application discloses a non-aqueous electrolyte for lithium-ion battery, comprising an unsaturated phosphate compound and a unsaturated cyclic carboxylic anhydride compound, the unsaturated phosphate compound having a structure represented by Structural Formula 4, Structural Formula 4 wherein $R_{13}$, $R_{11}$ and $R_{12}$ are each independently selected from a hydrocarbon group having 1 to 5 carbon atoms, and at least one of $R_{13}$, $R_{11}$ and $R_{12}$ is an unsaturated hydrocarbon group having a double bond or a triple bond; and the unsaturated cyclic carboxylic anhydride compound having a structure represented by Structural Formula 5, Structural Formula 5 wherein $R_{14}$ is selected from the group consisting of an alkenylene group having 2 to 4 carbon atoms or an fluorinated alkenylene group having 2 to 4 carbon atoms.

Generally, two kinds of additives with good high-temperature performance, high impedance and poor low-temperature performance, when used in combination, can allow the battery to further obtain better high-temperature performance, but the impedance will further increase and the low-temperature performance will further deteriorate. However, researchers in the art have found during researches that when adding the above-mentioned triple bond-containing phosphate compound and cyclic unsaturated carboxylic anhydride compound at the same time in a non-aqueous electrolyte for lithium-ion battery, in contrast to using the triple bond-containing phosphate compound alone, the high-temperature performance significantly improved, and unexpectedly, the interfacial impedance remarkably lowered, and the low-temperature performance remarkably improved.

The technical principle underlying adding an unsaturated phosphate compound and a cyclic unsaturated carboxylic anhydride compound at the same time is that during the first charging process, the unsaturated phosphate compound forms a film on the anode, and the passivation film formed by such compound on the anode has poor conductivity, which will significantly increase the impedance of the anode, resulting in the battery having an significantly higher overall impedance and a poor low-temperature performance; and the unsaturated cyclic carboxylic anhydride compound also has a very strong film-forming function on the anode during the first charging process, mainly in that such compound has a relatively higher film-forming potential on the anode and can take precedence over the unsaturated phosphate compound in forming a film on the anode, thus suppressing subsequent film formation of the unsaturated phosphate compound on the anode, and thereby decreasing battery impedance. In the present application, the unsaturated phosphate compound and the unsaturated cyclic carboxylic anhydride compound are used together and work in synergy to produce special effects not achievable when either of them is used alone.

Figure 1:
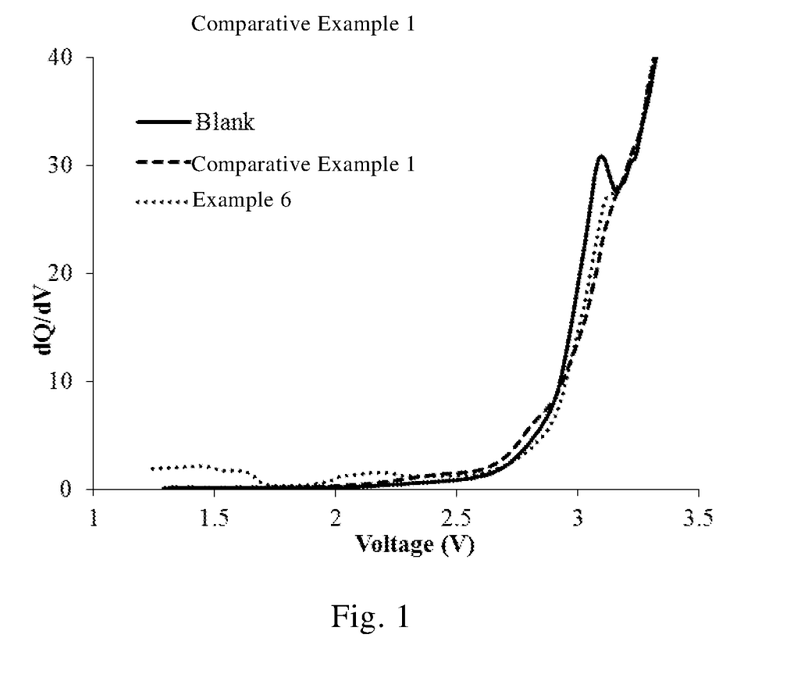
FIG. 1 is a capacity differential graph for the initial charging of a blank electrolyte, Example 6 and Comparative Example 1.
Figure 2:
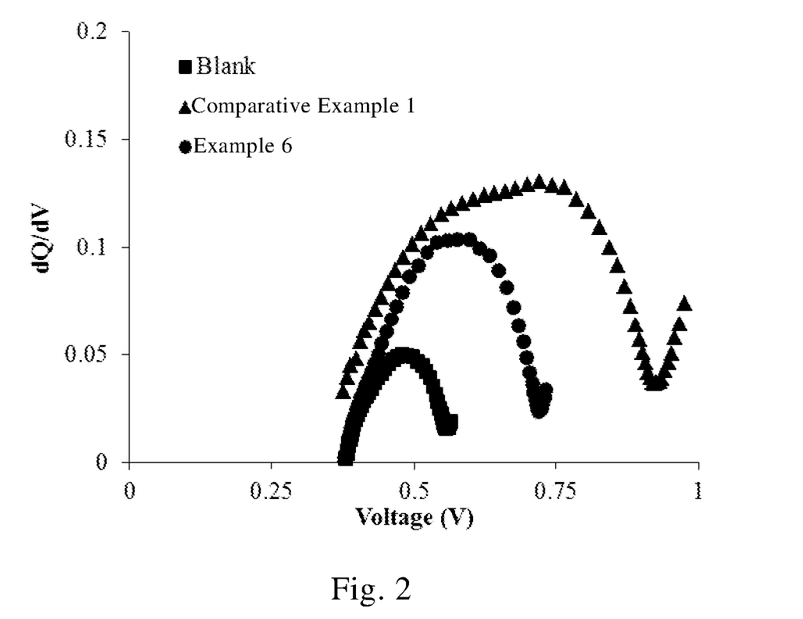
FIG. 2 is an alternating current impedance graph of a blank electrolyte, Example 6 and Comparative Example 1.

In light of the above description, the technical principle of simultaneously adding an unsaturated phosphate compound and a cyclic unsaturated carboxylic anhydride compound can be illustrated by FIG. 1 and FIG. 2, wherein "Blank" in the figures is a blank electrolyte: EC/EMC/DEC=1/1/1 (volume ratio), LiPF6: 1M. It can be seen from FIG. 1 and FIG. 2 that the unsaturated phosphate (Compound 1) starts film formation on the anode at about 2.7 V during the first charging process, which film formation on the anode will result in significantly increased impedance of the anode; and when the cyclic unsaturated carboxylic anhydride compound (CA) is added in addition to the unsaturated phosphate (Compound 1), the cyclic unsaturated carboxylic anhydride compound (CA) will preferentially forms a film on the surface of the anode at about 1.5 V and 2 V, and the film preferentially formed by the cyclic unsaturated carboxylic anhydride compound (CA) will suppress the subsequent film formation of the unsaturated phosphate (Compound 1) at 2.7 V, thus lowering the impedance of the anode.

Specifically, the unsaturated phosphate compound represented by the above Structural Formula 4 may be selected from the group consisting of the compounds of the following structural formulas

Compound 1

Compound 2

Compound 3

Compound 4

Compound 5

Compound 6

It is appreciated that both the unsaturated phosphate compound represented by Structural Formula 4 and the unsaturated phosphate compound represented by Compound 1 to Compound 6 are preferred technical solutions of the present application, without the exclusion of other saturated phosphate compounds having similar physical and chemical properties.

Specifically, the cyclic unsaturated carboxylic anhydride represented by the above Structural Formula 5 may be one or more selected from the group consisting of maleic anhydride (abbreviated as MA) and 2-methylmaleic anhydride (abbreviated as CA)

It is appreciated that the cyclic unsaturated carboxylic anhydride compound represented by the above Structural Formula 5, the MA and the CA are all preferred technical solutions of the present application, without the exclusion of other cyclic unsaturated carboxylic anhydride compounds having similar physical and chemical properties.

Preferably, in the non-aqueous electrolyte for lithium-ion battery according to the present application, the unsaturated phosphate compound accounts for 0.1% to 3%, more preferably 0.1% to 2% of the total weight of the non-aqueous electrolyte for lithium-ion battery.

It can be seen from the above description that when the content of the unsaturated phosphate compound is less than 0.1%, the film forming effect on the cathode is deteriorated, the protective effect on the cathode is lowered, and the effect of improving the performances is lowered; and when the content is more than 2%, the film formation at the electrode interface tends to be thick, which increases the electrode interface impedance, especially the anode interface impedance, thus increasing the overall impedance of the battery and deteriorating the battery performances.

Preferably, in the non-aqueous electrolyte for lithium-ion battery according to the present application, the cyclic unsaturated carboxylic anhydride compound accounts for 0.1% to 3%, more preferably 0.1% to 2% of the total weight of the non-aqueous electrolyte for lithium-ion battery.

Also, it is understood from the above description that when the content of the unsaturated cyclic carboxylic anhydride compound is less than 0.1%, the film forming effect on the anode is deteriorated, and it is difficult to effectively prevent the unsaturated phosphate compound from forming a film on the anode; and when the content of the cyclic carboxylic anhydride compound is more than 2%, the film formation at the electrode interface also tends to be thick, which increases the electrode interface impedance, especially the anode interface impedance, thus increasing the overall impedance of the battery and deteriorating the battery performances.

Further, the non-aqueous electrolyte for lithium-ion battery according to the present application further comprises at least one selected from the group consisting of an unsaturated cyclic carbonate or a cyclic sultone or a cyclic sulfate.

Further, the unsaturated cyclic carbonate compound accounts for 0.1% to 5% of the total weight of the non-aqueous electrolyte, the cyclic sultone compound accounts for 0.1% to 5% of the total weight of the non-aqueous electrolyte, and the cyclic sulfate compound accounts for 0.1% to 5% of the total weight of the non-aqueous electrolyte.

Further, the unsaturated cyclic carbonate is at least one selected from the group consisting of vinylene carbonate and vinylethylene carbonate.

The cyclic sultone is at least one selected from the group consisting of 1,3-propane sultone, 1,4-butane sultone, 1,3-propene sultone and methylene methanedisulfonate.

The cyclic sulfate is one or both selected from the group consisting of vinyl sulfate and propylene sulfate The non-aqueous electrolyte of the present application comprises a non-aqueous organic solvent, the organic solvent being at least one selected from the group consisting of ethylene carbonate, propylene carbonate, butylene carbonate, dimethyl carbonate, diethyl carbonate, methyl ethyl carbonate and methyl propylene carbonate.

Further, in the non-aqueous electrolyte of the present application, the lithium salt is at least one selected from the group consisting of lithium hexafluorophosphate, lithium tetrafluoroborate, lithium bis(trifluoromethylsulfonyl)imide, and lithium bisfluorosulfonimide.

Another aspect of the present application discloses a lithium-ion battery, comprising a cathode, an anode, a separator interposed between the cathode and the anode, and an electrolyte, wherein the electrolyte is the non-aqueous electrolyte for lithium-ion battery according to the present application.

The lithium-ion battery of the present application has a charge cut-off voltage of greater than or equal to 4.3V.

Further, in the lithium-ion battery of the present application, the cathode is at least one selected from the group consisting of $LiCoO_2$, $LiNiO_2$, $LiMn_2O_4$, $LiCo_{1-y}M_yO_2$, $LiNi_{1-y}M_yO_2$, $LiMn_{2-y}M_yO_4$ and $LiNi_xCo_yMn_zM_{1-x-y-z}O_2$; wherein M is at least one selected from the group consisting of Fe, Co, Ni, Mn, Mg, Cu, Zn, Al, Sn, B, Ga, Cr, Sr, V, and Ti, and $0 \leq y \leq 1$, $0 \leq x \leq 1$, $0 \leq z \leq 1$, and $x+y+z \leq 1$.

It should be noted that the non-aqueous electrolyte of the present application can be used in various lithium-ion batteries, including but not limited to the types listed in the present application.

Technical Solution II:

At present, lithium-ion battery electrolytes use carbonate as a solvent. When the charging voltage of the lithium-ion battery is greater than 4.2V, the carbonate solvent is oxidized and decomposes on the surface of the cathode material to generate gas and other decomposition products. On the one hand, the gas generated will cause the battery to bulge, which poses safety hazard to the battery. On the other hand, the decomposition products will obviously increase the impedance of the battery, thereby degrading the performances of the battery. Therefore, for a high-voltage lithium-ion battery, it is necessary to develop a solvent having a higher oxidation potential than the carbonate. According to literature report (Electrochemistry Communications 44 (2014) 34-37), fluorocarbonate can significantly improve the high-temperature cycling performance of high-voltage lithium-ion batteries. However, the present Applicant has found that although fluorocarbonate can improve the high-temperature cycling performance, gas production in the battery is serious during high-temperature storage, which poses a safety hazard. Chinese Patent Application No. CN104704657A discloses an electrolyte comprising a fluorinated carboxylate, which can improve the high-temperature cycling performance of the high-voltage lithium-ion battery. Nevertheless, the present Applicant has found that the fluorinated carboxylate has poor compatibility with the carbon anode material, and will be reduced and decompose to generate a large amount of gas on the surface of the anode during the charging process of the battery, which poses a great safety hazard to the battery and significantly degrades the performances of the battery. Chinese Patent No. 201410534841.0 discloses a triple bond-containing phosphate compound as a novel film-forming additive, which not only improves the high-temperature cycling performance, but also significantly improves the storage performance. However, researchers in the art have found during researches that the passivation film formed by the triple bond-containing phosphate additive at the electrode interface has poor conductivity, resulting in high interface impedance, significantly degrading the low-temperature performance, and restricting the application of the lithium-ion batteries containing non-aqueous electrolyte under low temperature conditions. Patent literature reports that cyclic carboxylic anhydrides can improve the high-temperature storage performance. However, the present inventors have found that in an electrolyte with carbonate as a solvent, cyclic carboxylic anhydrides significantly increase the impedance of the battery and degrade the low-temperature discharge performance and the rate performance of the battery.

In this regard, an aspect of the present application discloses a non-aqueous electrolyte for lithium-ion battery, comprising Component A and Component B; wherein Component A includes at least one selected from the group consisting of the fluorinated cyclic carbonates represented by Structural Formula 1, and also includes at least one selected from the group consisting of the alkyl-substituted cyclic carbonates represented by Structural Formula 2 and/or at least one selected from the group consisting of the fluorinated carboxylates represented by Structural Formula 3;

Structural Formula 1 wherein $R_1$ is a fluorine element or a fluorine-containing hydrocarbon group having 1 to 4 carbon atoms, and $R_2$, $R_3$ and $R_4$ are each independently selected from a hydrogen element, a fluorine element, a hydrocarbon group having 1 to 4 carbon atoms or a fluorine-containing hydrocarbon group having 1 to 4 carbon atoms;

Structural Formula 2 wherein $R_5$ is a hydrocarbon group having 1 to 4 carbon atoms, and $R_6$, $R_7$ and $R_8$ are each independently selected from a hydrogen element or a hydrocarbon group having 1 to 4 carbon atoms;

Structural Formula 3: $R_9COOR_{10}$, wherein $R_9$ and $R_{10}$ are each independently selected from a hydrocarbon group having 1 to 4 carbon atoms or a fluorohydrocarbon group having 1 to 4 carbon atoms, and at least one of $R_9$ and $R_{10}$ is the fluorohydrocarbon group; and the fluorohydrocarbon group contains at least two fluorine atoms;

Structural Formula 4 wherein $R_{11}$ is an unsaturated hydrocarbon group having 1 to 4 carbon atoms, and $R_{12}$ and $R_{13}$ are each independently selected from a saturated hydrocarbon group having 1 to 4 carbon atoms, an unsaturated hydrocarbon group having 1 to 4 carbon atoms or a fluorohydrocarbon group having 1 to 4 carbon atoms;

Structural Formula 5 wherein $R_{14}$ is selected from the group consisting of an alkylene group or alkenylene group having 2 to 4 carbon atoms, or a fluorine-containing alkylene group or fluorine-containing alkenylene group having 2 to 4 carbon atoms.

It should be noted that the key of the non-aqueous electrolyte of the present application lies in that Component A and Component B are used in combination and work in synergy. The fluorocarbonate and the fluorocarboxylate in Component A can increase the oxidative decomposition potential of the electrolyte, because the oxidation resistance of the fluorocarbonate and the fluorocarboxylate is higher than that of the carbonate. Further, the fluorocarbonate and the fluorocarboxylate can form a passivation film on the surface of the anode, thereby suppressing the decomposition reaction of the electrolyte. However, with regard to the fluorocarbonate solvent, during high-temperature storage of the battery, the thermal stability of the passivation film is not ideal, and a large amount of gas is generated, which lowers the high-temperature storage performance of the battery. With regard to the fluorocarboxylate solvent, it will decompose on the surface of the anode to produce a large amount of gas during the first charging of the battery, resulting in poor contact between the electrode plates, thereby degrading the performances of the battery. Although the unsaturated phosphate or cyclic carboxylic anhydride of Component B can form a passivation film on the surface of the cathode and the anode, the internal resistance of the battery is remarkably increased, and the low-temperature performance of the battery is remarkably lowered. When Component A and Component B are used at the same time in the present application, while Component A undergoes a film-forming reaction on the surface of the cathode and the anode, Component B also participates in the film-forming reaction on the cathode and the anode, such that the components of the passivation layers on the cathode and the anode includes both the decomposition products of Component A and the decomposition products of Component B, which improves the interfaces of the cathode and the anode. This not only improves the thermal stability of the passivation film on the anode, thus ensuring the high-temperature performance of the battery, but also will not significantly increase the impedance of the battery, thus ensuring the low-temperature performance of the battery. In the present application, Component A and Component B are used together and work in synergy to produce special effects not achievable when either of them is used alone.

In the above electrolyte, Component A accounts for 10-90% of the total weight of the non-aqueous electrolyte, and Component B accounts for 0.1-3% of the total weight of the non-aqueous electrolyte.

In the present invention, the compound represented by Structural Formula 1 is a necessary component and is used together with the substance represented by Structural Formula 2 and/or Structural Formula 3 as the solvent. That is, according to the present invention, Component A may be a compound represented by Structural Formula 1 and a compound represented by Structural Formula 2, or a compound represented by Structural Formula 1 and a compound of Structural Formula 3. Also, a compound represented by Structural Formula 1 and a compound represented by Structural Formula 2 and a compound represented by Structural Formula 3 can be used together as Component A.

Preferably, the compound represented by Structural Formula 1 accounts for 5% to 80% of the total weight of the non-aqueous electrolyte.

When the compound represented by Structural Formula 2 is present in Component A, it is preferred that the compound represented by Structural Formula 2 accounts for 5% to 80%, more preferably 5 to 30% of the total weight of the non-aqueous electrolyte. When the compound represented by Structural Formula 3 is present in Component A, it is preferred that the compound represented by Structural Formula 3 accounts for 5% to 80%, more preferably 20 to 70% of the total weight of the non-aqueous electrolyte.

In the present invention, Component B is the compound represented by Structural Formula 4 and/or the compound represented by Structural formula 5. When the compound represented by Structural Formula 4 is present in Component B, it is preferred that the compound represented by Structural Formula 4 accounts for 0.1% to 3% of the total weight of the non-aqueous electrolyte. When the compound represented by Structural Formula 5 is present in Component B, it is preferred that the compound represented by Structural Formula 5 accounts for 0.1% to 3% of the total weight of the non-aqueous electrolyte.

Preferably, the unsaturated cyclic carbonate is at least one selected from the group consisting of vinylene carbonate and vinylethylene carbonate.

Preferably, the compound represented by Structural Formula 1 is a fluorinated cyclic carbonate. Preferably, the compound represented by Structural Formula 1 is one or more selected from the group consisting of the compounds of the following structural formulas:

(Formula 1-1, abbreviated as FEC)

(Formula 1-2, abbreviated as DFEC)

(Formula 1-3)

(Formula 1-4)

Preferably, the compound represented by Structural Formula 2 is an alkyl-substituted cyclic carbonate. Preferably, the compound represented by Structural Formula 2 is one or more selected from the group consisting of the compounds of the following structural formulas:

(Formula 2-1, abbreviated as PC)

(Formula 2-2)

(Formula 2-3)

Preferably, in Structural Formula 3, the hydrocarbon group having 1 to 5 carbon atoms is selected from the group consisting of methyl, ethyl, propyl, and butyl group; and the fluorohydrocarbon group is selected from the group consisting of fluoromethyl, fluoroethyl, fluoropropyl, and fluorobutyl group.

Preferably, the fluorocarboxylate compound represented by Structural Formula 3 is one or more selected from the group consisting of $H_3CCOOCH_2CF_2H$ (3-1, abbreviated as DFEA), $H_3CH_2CCOOCH_2CF_2H$ (3-2, abbreviated as DFEP), $HF_2CH_2CCOOCH_3$ (3-3, abbreviated as MDFP), $HF_2CH_2CCOOCH_2CH_3$ (3-4, abbreviated as EDFP), $HF_2CH_2CH_2CCOOCH_2CH_3$ (3-5, abbreviated as EDFB), $H_3CCOOCH_2CH_2CF_2H$ (3-6, abbreviated as DFPA), $H_3CH_2CCOOCH_2CH_2CF_2H$ (3-7, abbreviated as DFPP), $CH_3COOCH_2CF_3$ (3-8, abbreviated as TFEA), $HCOOCH_2CHF_2$ (3-9, abbreviated as DFEF), $HCOOCH_2CF_3$, $CH_3COOCH_2CF_2CF_2H$ (3-10, abbreviated as TFPA).

Preferably, the saturated hydrocarbon group having 1 to 4 carbon atoms in Structural Formula 4 includes, but is not limited to, methyl, ethyl, and propyl group; the unsaturated hydrocarbon group having 1 to 4 carbon atoms includes, but is not limited to, vinyl, allyl, 3-butenyl, isobutenyl, ethynyl, propargyl, 3-butynyl, and 1-methyl-2-propynyl group; and the halohydrocarbon group includes, but is not limited to difluoromethyl, trifluoromethyl, 2,2-difluoroethyl, 2,2,2-trifluoroethyl, 3,3-difluoropropyl, 3,3,3-trifluoropropyl, and hexafluoroisopropyl group.

Preferably, the unsaturated phosphate compound represented by Structural Formula 4 is one or more selected from the group consisting of tripropargyl phosphate (4-1), dipropargyl methyl phosphate (4-2), dipropargylethyl phosphate (4-3), dipropargylpropyl phosphate (4-4), dipropargyl trifluoromethyl phosphate (4-5), dipropargyl 2,2,2-trifluoroethyl phosphate (4-6), dipropargyl 3,3,3-trifluoropropyl phosphate (4-7), dipropargyl hexafluoroisopropyl phosphate (4-8), triallyl phosphate (4-9), diallyl methyl phosphate (4-10), diallyl ethyl phosphate (4-11), diallyl propyl phosphate (4-12), diallyl trifluoromethyl phosphate (4-13), diallyl 2,2,2-trifluoroethyl phosphate (4-14), diallyl 3,3,3-trifluoropropyl phosphate (4-15) and diallyl hexafluoroisopropyl phosphate (4-16).

Preferably, the cyclic carboxylic anhydride represented by Structural Formula 5 is one or more selected from the group consisting of succinic anhydride (5-1, abbreviated as SA), maleic anhydride (5-2, abbreviated as MA), 2-methylmaleic anhydride (5-3, abbreviated as CA).

Preferably, the non-aqueous electrolyte further comprises at least one selected from the group consisting of an unsaturated cyclic carbonate, a cyclic sultone, and a cyclic sulfate.

Preferably, the unsaturated cyclic carbonate compound accounts for 0.1% to 5% of the total weight of the non-aqueous electrolyte, the cyclic sultone compound accounts for 0.1% to 5% of the total weight of the non-aqueous electrolyte, and the cyclic sulfate compound accounts for 0.1% to 5% of the total weight of the non-aqueous electrolyte.

Preferably, the unsaturated cyclic carbonate is at least one selected from the group consisting of vinylene carbonate and vinylethylene carbonate.

Preferably, the cyclic sulfate is at least one selected from the group consisting of:

(abbreviated as DTD)    (abbreviated as TS)

Preferably, the cyclic sultone is at least one selected from the group consisting of 1,3-propane sultone (abbreviated as PS), 1,4-butane sultone (abbreviated as BS), and 1,3-propene sultone (abbreviated as PST), methylene methanedisulfonate (abbreviated as MMDS).

Preferably, the non-aqueous electrolyte further comprises at least one selected from the group consisting of ethylene carbonate, propylene carbonate, butylene carbonate, dimethyl carbonate, diethyl carbonate, methyl ethyl carbonate, and methyl propyl carbonate. The content thereof may vary within a wide range, and preferably, the content thereof accounts for 1% to 40% of the total weight of the non-aqueous electrolyte. It is appreciated that when a plurality of the above substances are present, the above content range refers to that for the total content of the plurality of the above substances.

Another aspect of the present application discloses a lithium-ion battery, comprising a cathode, an anode, a separator interposed between the cathode and the anode, and an electrolyte, wherein the electrolyte is the non-aqueous electrolyte for lithium-ion battery according to the present application.

Preferably, the cathode active material is at least one selected from the group consisting of $LiNi_xCo_yMn_zL_{(1-x-y-z)}O_2$, $LiCo_xL_{(1-x)}O_2$ and $LiNi_{x'}L'_{y'}Mn_{(2-x''-y')}O_4$, wherein L is Al, Sr, Mg, Ti, Ca, Zr, Zn, Si or Fe, $0 \leq x \leq 1$, $0 \leq y \leq 1$, $0 \leq z \leq 1$, $0 < x+y+z \leq 1$, $0 < x' \leq 1$, $0.3 \leq x'' \leq 0.6$, and $0.01 \leq y' \leq 0.2$, and L' is Co, Al, Sr, Mg, Ti, Ca, Zr, Zn, Si or Fe.

Technical Solution III:

At present, lithium-ion battery electrolytes use carbonate as a solvent. When the charging voltage of the lithium-ion battery is greater than 4.2V, the carbonate solvent is oxidized and decomposes on the surface of the cathode material to generate gas and other decomposition products. On the one hand, the gas generated will cause the battery to bulge, which poses safety hazard to the battery. On the other hand, the decomposition products will obviously increase the impedance of the battery, thereby degrading the performances of the battery. Therefore, for a high-voltage lithium-ion battery, it is necessary to develop a solvent having a higher oxidation potential than the carbonate. Chinese Patent Application No. CN104704657A discloses an electrolyte comprising a fluorinated carboxylate and a phosphate, which can improve the high-temperature cycling performance of the high-voltage lithium-ion battery. Nevertheless, the present Applicant has found that the fluorinated carboxylate has poor compatibility with the carbon anode material, and will be reduced and decompose to generate a large amount of gas on the surface of the anode during the charging process of the battery, which poses a great safety hazard to the battery and significantly degrades the performances of the battery. Although the phosphate can inhibit the decomposition of the fluorocarboxylate to a certain extent, the high-temperature cycling and high-temperature storage performance need to be further improved.

In this regard, another aspect of the present application discloses a non-aqueous electrolyte for lithium-ion battery, comprising at least one selected from the group consisting of a first compounds represented by Structural Formula 3 and at least one selected from the group consisting of a second compounds represented by Structural Formula 4;

Structural Formula 3: $R_9COOR_{10}$, wherein $R_9$ and $R_{10}$ are each independently selected from a hydrocarbon group or a fluorinated hydrocarbon group having 1 to 5 carbon atoms, and at least one of $R_9$ and $R_{10}$ is the fluorinated hydrocarbon group; and the fluorinated hydrocarbon group has at least two hydrogen atoms substituted by fluorine;

Structural Formula 4 wherein $R_{11}$, $R_{12}$ and $R_{13}$ are each independently selected from a saturated hydrocarbon group, an unsaturated hydrocarbon group or a halogenated hydrocarbon group having 1 to 5 carbon atoms, and at least one of $R_{11}$, $R_{12}$ and $R_{13}$ is an unsaturated hydrocarbon group.

It should be noted that the key of the non-aqueous electrolyte of the present application lies in that the first compounds represented by Structural Formula 3 and the second compounds represented by Structural Formula 4 are used in combination and work in synergy. The first compounds, due to the high oxidation potential, can reduce the decomposition reaction of the electrolyte on the surface of the high-voltage cathode material, but the first compounds will decompose on the surface of the anode, thereby generating a large amount of gas, which poses a safety hazard. The second compounds, due to the unsaturated bond present in the molecular structure, can undergo a polymerization reaction on the material surface of the cathode and the anode to form a passivation film during the initial charging process of the lithium-ion battery, but the passivation film has a high impedance, which lowers the low-temperature discharge performance and the rate performance of the battery. When the first compounds and the second compounds are used together in the present application, the second compounds preferentially undergo a polymerization reaction to form a passivation film on the surface of the anode, which can inhibit the decomposition reaction of the first compounds on the surface of the anode, thereby suppressing gas generation from decomposition of the first compounds on the surface of the anode during the charging process. In addition, the first compounds can also partially participate in the film-forming reaction on the anode, thereby improving the interface of the anode. The first compounds and the second compounds are used together and work in synergy to produce special effects not achievable when either of them is used alone.

In the present application, the first compounds and the second compounds are used together; wherein the first compounds can be added in a conventional amount, for example, preferably, the first compounds account for 10% to 80% of the total weight of the non-aqueous electrolyte; the second compound may be used in an amount according to the conventional amounts of the additives for non-aqueous electrolytes, for example, about 0.8-1.2% of the total weight of the non-aqueous electrolyte, or generally, 0.01%-5% of the total weight of the non-aqueous electrolyte. The first compounds may be used alone as a non-aqueous organic solvent for the non-aqueous electrolyte, or may be used in combination with other common organic solvents, which will be described in detail hereinafter.

It should also be noted that the key to the present application lies in the use of the first compounds and the second compounds in the non-aqueous electrolyte. As for other conventional components, such as lithium salts, reference may be made to existing non-aqueous electrolytes, and further, other commonly used reagents may be added to the non-aqueous electrolyte to enhance the corresponding functions, which are not specifically limited herein. However, in the preferred embodiments of the present application, in order to achieve a better effect, other organic solvents than the non-aqueous organic solvent, lithium salts and other reagents are specifically defined, which will be described in detail hereinafter.

Preferably, in the Structural Formula 1, the hydrocarbon group having 1 to 5 carbon atoms includes, but is not limited to, methyl, ethyl, propyl, vinyl, allyl, 3-butenyl, isobutenyl, 4-pentenyl, ethynyl, propargyl, 3-butynyl, 1-methyl-2-propynyl; and the fluorohydrocarbon group includes, but is not limited to, difluoromethyl, trifluoromethyl, 2,2-difluoroethyl, 2,2,2-trifluoroethyl, 3,3-difluoropropyl, 3,3,3-trifluoropropyl, and hexafluoroisopropyl;

In Structural Formula 2, the saturated hydrocarbon group having 1 to 5 carbon atoms includes, but is not limited to, methyl, ethyl, and propyl group; the unsaturated hydrocarbon group having 1 to 5 carbon atoms includes, but is not limited to, vinyl, allyl, 3-butenyl, isobutenyl, 4-pentenyl, ethynyl, propargyl, 3-butynyl, 1-methyl-2-propynyl group; and the halogenated hydrocarbon group having 1 to 5 carbon atoms includes, but is not limited to, difluoromethyl, trifluoromethyl, 2,2-difluoroethyl, 2,2,2-trifluoroethyl, 3,3-difluoropropyl, 3,3,3-trifluoropropyl, and hexafluoroisopropyl group.

Preferably, the first compounds are selected from $H_3CCOOCH_2CF_2H$ (3-1, abbreviated as DFEA), $H_3CH_2CCOOCH_2CF_2H$ (3-2, abbreviated as DFEP), $HF_2CH_2CCOOCH_3$ (3-3, abbreviated as MDFP), $HF_2CH_2CCOOCH_2CH_3$ (3-4, abbreviated as EDFP), $HF_2CH_2CCOOCH_2CH_3$ (3-5, abbreviated as EDFB), $H_3CCOOCH_2CH_2CF_2H$ (3-6, abbreviated as DFPA), $H_3CH_2CCOOCH_2CH_2CF_2H$ (3-7, abbreviated as DFPP), $CH_3COOCH_2CF_3$ (3-8, abbreviated as TFEA), $HCOOCH_2CHF_2$ (3-9, abbreviated as DFEF), $HCOOCH_2CF_3$, $CH_3COOCH_2CF_2CF_2H$ (3-10, abbreviated as TFPA).

Preferably, the second compounds are at least one selected from the group consisting of tripropargyl phosphate, dipropargyl methyl phosphate, dipropargyl ethyl phosphate, dipropargyl propyl phosphate, dipropargyl trifluoromethyl phosphate, dipropargyl 2,2,2-trifluoroethyl phosphate, dipropargyl 3,3,3-trifluoropropyl phosphate, dipropargyl hexafluoroisopropyl phosphate, triallyl phosphate, diallyl methyl phosphate, diallyl ethyl phosphate, diallyl propyl phosphate, diallyl trifluoromethyl phosphate, diallyl 2,2,2-trifluoroethyl phosphate, diallyl 3,3,3-trifluoropropyl phosphate or diallyl hexafluoroisopropyl phosphate.

Preferably, the non-aqueous electrolyte further comprises one or more selected from the group consisting of an unsaturated cyclic carbonate, an unsaturated acid anhydride, a cyclic sulfate, a cyclic sultone and a sulfone.

The unsaturated cyclic carbonate includes at least one selected from the group consisting of vinylene carbonate (abbreviated as VC) and vinylethylene carbonate (abbreviated as VEC);

Preferably, the cyclic sultone includes at least one selected from the group consisting of 1,3-propane sultone (abbreviated as 1,3-PS), 1,4-butane sultone (abbreviated as BS), 1,3-propene sulfone (abbreviated as PST) and methylene methanedisulfonate (abbreviated MMDS).

Preferably, the unsaturated acid anhydride includes at least one selected from the group consisting of succinic anhydride (abbreviated as SA), maleic anhydride (abbreviated as MA), and 2-methylmaleic anhydride (CA).

Preferably, the cyclic sulfate comprises one or both selected from the group consisting of vinyl sulfate (abbreviated as DTD) and propylene sulfate (abbreviated as TS).

Preferably, the sulfone includes sulfolane (abbreviated as SL).

It should be noted that vinylene carbonate (abbreviated as VC), vinylethylene carbonate (abbreviated as VEC), fluoroethylene carbonate (abbreviated FEC), or 1,3-propane sultone (abbreviated as 1,3PS), 1,4-butane sultone (abbreviated as BS), 1,3-propene sultone (abbreviated as PST), methylene methanedisulfonate (abbreviated as MMDS), succinic anhydride (abbreviated SA), maleic anhydride (abbreviated as MA), 2-methylmaleic anhydride (abbreviated as CA), vinyl sulfate (abbreviated DTD), propylene sulfate (abbreviated as TS), sulfolane (abbreviated as SL) and 1,4-butyrolactone (abbreviated as GBL) are all conventional reagents reported for non-aqueous electrolytes. Some of these reagents can be used as an additive or as a solvent, such as FEC, which can be regarded as an solvent when used in a relatively large amount, and can be regarded as an additive when used in a relatively small amount. For example, in the present invention, preferably, VC accounts for 0.1% to 4%, more preferably 0.5% to 1.5% of the total weight of the non-aqueous electrolyte; VEC accounts for 0.1% to 3%, more preferably 0.2% to 1.5% of the total weight of the non-aqueous electrolyte; 1,3-PS accounts for 0.1% to 10%, more preferably 1% to 3% of the total weight of the non-aqueous electrolyte; BS accounts for 0.1% to 10%, more preferably 1% to 3% of the total weight of the non-aqueous electrolyte; PST accounts for 0.1% to 3%, more preferably 0.5% to 2% of the total weight of the non-aqueous electrolyte; MMDS accounts for 0.1% to 4%, more preferably 0.5% to 2% of the total weight of the non-aqueous electrolyte; SA accounts for 0.1% to 4%, more preferably 0.5% to 2% of the total weight of the non-aqueous electrolyte; MA accounts for 0.1% to 4%, more preferably 0.5% to 2% of the total weight of the non-aqueous electrolyte; CA accounts for 0.1% to 4%, more preferably 0.5% to 2% of the total weight of the non-aqueous electrolyte; DTD accounts for 0.1% to 5%, more preferably 0.5% to 3% of the total weight of the non-aqueous electrolyte; TS accounts for 0.1% to 4%, more preferably 0.5% to 3% of the total weight of the non-aqueous electrolyte; SL accounts for 0.1% to 30%, more preferably 2 to 15% of the total weight of the non-aqueous electrolyte; and GBL accounts for 0.1% to 30%, more preferably 2 to 15% of the total weight of the non-aqueous electrolyte.

Preferably, the non-aqueous electrolyte further comprises at least one selected from the group consisting of ethylene carbonate, fluoroethylene carbonate (abbreviated as FEC), propylene carbonate, butylene carbonate, dimethyl carbonate, diethyl carbonate, methyl ethyl carbonate, and methyl propyl carbonate. The content thereof may vary within a wide range, and preferably, the content thereof accounts for 1% to 40% of the total weight of the non-aqueous electrolyte. It is appreciated that when a plurality of the above substances are present, the above content range refers to that for the total content of the plurality of the above substances.

More preferably, the non-aqueous electrolyte further comprises at least one selected from the group consisting of ethylene carbonate, fluoroethylene carbonate and propylene carbonate.

Another aspect of the present application discloses a use of the non-aqueous electrolyte of the present application in a lithium-ion battery or a storage capacitor.

Another aspect of the present application discloses a lithium-ion battery, comprising a cathode, an anode, a separator interposed between the cathode and the anode, and an electrolyte, wherein the electrolyte is the non-aqueous electrolyte for lithium-ion battery according to the present application.

It is appreciated that the key of the lithium-ion battery of the present application lies in the use of the non-aqueous electrolyte of the present application, so that a passivation film is formed on the surface of the cathode and the anode, thereby effectively inhibiting the decomposition reaction of the electrolyte on the surface of the cathode and the anode, suppressing the destruction of the structure of the cathode material, reducing lithium precipitation, thus ensuring the high- and low-temperature performances and the rate performance of the battery. As for other components in the lithium-ion battery, such as the cathode, the anode and the separator, reference may be made to conventional lithium-ion batteries. In preferred embodiments of the present application, the cathode active material is specifically defined.

Preferably, the cathode active material is at least one selected from the group consisting of $LiNi_xCo_yMn_zL_{(1-x-y-z)}O_2$, $LiCo_xL_{(1-x')}O_2$ and $LiNi_{x'}L'_{y'}Mn_{(2-x''-y')}O_4$, wherein L is Al, Sr, Mg, Ti, Ca, Zr, Zn, Si or Fe, $0 \leq x \leq 1$, $0 \leq y \leq 1$, $0 \leq z \leq 1$, $0 < x+y+z \leq 1$, $0 < x' \leq 1$, $0.3 \leq x'' \leq 0.6$, and $0.01 \leq y' \leq 0.2$, and L' is Co, Al, Sr, Mg, Ti, Ca, Zr, Zn, Si or Fe.

Due to the adoption of the above technical solutions, the present application has the following beneficial effects:

In the non-aqueous electrolyte of the present application, the first compounds represented by Structural Formula 1 and the second compounds represented by Structural Formula 2 are used in combination and work in synergy, which not only improves the high-temperature cycling performance of the high-voltage lithium-ion battery, but also avoids gas generation due to decomposition on the surface of the anode. Moreover, the first compounds can also partially participate in the film forming reaction on the anode, thereby improving the interface of the anode and ensuring the low-temperature discharge performance and the rate performance of the battery.

DETAILED DESCRIPTION OF THE INVENTION

The present application will be further described in detail below by reference to particular examples and the accompanying drawings. The following examples are only intended to further illustrate the application and are not to be construed as limiting the invention.

Examples

Technical Solution I:

In this technical solution, electrolytes were prepared according to the components and ratios shown in Table 1. A plurality of non-aqueous electrolytes for lithium-ion battery according to the present application as well as a plurality of Comparative Examples were designed, as shown in Table 1 in detail.

In this technical solution, lithium hexafluorophosphate was used as the lithium salt. It is appreciated that the lithium salt used in this technical solution served only as a particular embodiment. Other lithium salts used in the art, such as $LiBF_4$, LiBOB, LiDFOB, $LiPO_2F_2$, $LiSbF_6$, $LiAsF_6$, $LiN(SO_2CF_3)_2$, $LiN(SO_2C_2F_5)_2$, $LiC(SO_2CF_3)_3$ and $LiN(SO_2F)_2$, can also be used in this technical solution, and are not specifically limited herein.

The electrolytes in this technical solution were prepared by preparing a non-aqueous organic solvent according to a volume ratio of EC/EMC/DEC=1/1/1 (volume ratio), and then adding lithium hexafluorophosphate to the solvent to a final concentration of 1.0 mol/L, and then adding the additive according to Table 1. The percentage in Table 1 was percentage by weight, i.e., the percentage of the additive based on the total weight of the electrolyte.

TABLE 1

| | The components and their contents in the electrolytes | | |
|---|---|---|---|
| Example | Unsaturated phosphate compound | Unsaturated cyclic carboxylic anhydride and content thereof | Other additive and content thereof |
| Example 1 | Tripropargyl phosphate: 0.5% | CA: 0.1% | |
| Example 2 | Tripropargyl phosphate: 0.5% | CA: 0.5% | |
| Example 3 | Tripropargyl phosphate: 0.5% | CA: 1% | |
| Example 4 | Tripropargyl phosphate: 0.5% | CA: 2% | |
| Example 5 | Tripropargyl phosphate: 0.1% | CA: 0.5% | |
| Example 6 | Tripropargyl phosphate: 1% | CA: 0.5% | |
| Example 7 | Tripropargyl phosphate: 2% | CA: 0.5% | |
| Example 8 | Tripropargyl phosphate: 1% | CA: 0.1% | |
| Example 9 | Tripropargyl phosphate: 0.1% | CA: 1% | |

TABLE 1-continued

The components and their contents in the electrolytes

| Example | Unsaturated phosphate compound | Unsaturated cyclic carboxylic anhydride and content thereof | Other additive and content thereof |
|---|---|---|---|
| Example 10 | Tripropargyl phosphate: 0.5% | MA: 0.5% | |
| Example 11 | Tripropargyl phosphate: 0.5% | MA: 1% | |
| Example 12 | Tripropargyl phosphate: 0.5% | CA: 0.5% | Vinylene carbonate: 1% |
| Example 13 | Tripropargyl phosphate: 0.5% | CA: 0.5% | 1,3-propane sultone: 1% |
| Example 14 | Tripropargyl phosphate: 0.5% | CA: 0.5% | Vinyl sulfate: 1% |
| Example 15 | Diallylethyl phosphate: 0.5% | CA: 0.5% | |
| Example 16 | Diallylethyl phosphate: 1% | CA: 0.5% | |
| Example 17 | Diallylethyl phosphate: 2% | CA: 0.5% | |
| Example 18 | Diallylethyl phosphate: 1% | CA: 0.1% | |
| Comparative Example 1 | Tripropargyl phosphate: 1% | | |
| Comparative Example 2 | Diallylethyl phosphate: 1% | | |

In the lithium-ion batteries in this technical solution, the cathode active material used was $LiNi_{0.5}Co_{0.2}Mn_{0.3}O_2$, the anode used was artificial graphite, and the separator used was a three-layer separator of polypropylene, polyethylene and polypropylene. Specifically, lithium-ion batteries were made as follows.

Preparation of the cathode: Cathode active material $LiNi_{0.5}Co_{0.2}Mn_{0.3}O_2$, conductive carbon black and binder polyvinylidene fluoride were mixed in a mass ratio of 96.8:2.0:1.2. The mixture was dispersed in N-methyl-2-pyrrolidone to obtain a cathode slurry. The cathode slurry was uniformly coated onto both sides of an aluminum foil, which was then subjected to oven drying, calandering and vacuum drying, followed by welding of aluminum lead wires by an ultrasonic welder to obtain the cathode plate, the thickness of the plate being in the range of 120-150 μm.

Preparation of the anode: Graphite, conductive carbon black and binders styrene-butadiene rubber and carboxymethyl cellulose were mixed in a mass ratio of 96:1:1.2:1.8. The mixture was dispersed in deionized water to obtain an anode slurry. The anode slurry was coated onto both sides of a copper foil, which was then subjected to oven drying, calandering and oven drying, followed by welding of nickel lead wires by an ultrasonic welder to obtain the anode plate, the thickness of the plate being in the range of 120-150 μm.

Preparation of the separator: a three-layer separator of polypropylene, polyethylene and polypropylene was used, the thickness being 20 μm.

Battery assembling: the three-layer separator having a thickness of 20 μm was placed between the cathode plate and the anode plate, and the resulting sandwich structure composed of the cathode plate, the anode plate and the separator was wound. The wound structure was flattened and placed into an aluminum foil packing bag, and baked at 75° C. for 48 hours to obtain a battery core, which was to be injected with electrolyte. Then, the battery core was injected with an electrolyte prepared as above, and was vacuum-packed and allowed to stand for 24 hours.

Battery formation: 0.05 C constant current charging for 180 min, 0.1 C constant current charging to 3.95V, vacuum packing again and standing at 45° C. for 48 h, then further, 0.2 C constant current charging to 4.4V, and 0.2 C constant current discharging to 3.0V.

The batteries having the respective electrolytes in this technical solution were subjected to capacity retention rate test of 1 C cycling for 300 cycles at 45° C. and 1 C cycling for 500 cycles at normal temperature; capacity retention rate, capacity recovery rate, and thickness expansion rate tests after storage at 60° C. for 30 days; 1 C discharging efficiency test at −20° C.; and normal and low temperature direct current impedance test. The specific test methods are as follows:

(1) The capacity retention rate test of 1 C cycling for 300 cycles at 45° C. was in fact to measure the high-temperature cycling performance of the battery. The specific test method comprised: subjecting, at 45° C., the formed battery to 1 C constant current and constant voltage charging to 4.35V, with the cut-off current being 0.01 C, followed by 1 C constant current discharging to 3.0V. After 300 cycles of charging/discharging, the capacity retention rate at the $300^{th}$ cycle was calculated to evaluate the high-temperature cycling performance. The formula for calculating the capacity retention rate after 1 C cycling for 300 cycles at 45° C. is as follows:

Capacity retention rate at the $300^{th}$ cycle (%)=(discharge capacity at the $300^{th}$ cycle/discharge capacity at the $1^{st}$ cycle)×100%.

(2) Normal temperature cycling performance test: At 25° C., the formed battery was subjected to 1 C constant current constant voltage charging to 4.35 V, then 1 C constant current discharging to 3.0 V. The capacity retention rate at the $500^{th}$ cycle after 500 cycles of charging/discharging was calculated to evaluate the normal temperature cycling performance. The formula for calculation is as follows:

Capacity retention rate at the $500^{th}$ cycle (%)=(discharge capacity at the $500^{th}$ cycle/discharge capacity at the $1^{st}$ cycle)×100%.

(3) The test method of capacity retention rate, capacity recovery rate and thickness expansion rate after storage at 60° C. for 30 days comprised: subjecting, at a normal temperature, the formed battery to 1 C constant current constant voltage charging to 4.35 V, with the cut-off current being 0.01 C; followed by 1 C constant current discharging to 3.0 V, at which time the initial discharge capacity of the battery was measured, followed by 1 C constant current constant voltage charging to 4.35V, with the cut-off current being 0.01 C, at which time the initial thickness of the battery was measured; followed by storage of the battery at 60° C. for 30 days, at which time the thickness of the battery was measured; followed by 1 C constant current discharging to 3.0V, at which time the retention capacity of the battery was measured; followed by 1 C constant current constant voltage charging to 4.35V, with the cut-off current being 0.01 C; and followed by 1 C constant current discharging to 3.0 V, at which time the recovery capacity was measured.

The formulas for calculating the capacity retention rate, capacity recovery rate, and thickness expansion rate are as follows:

Battery capacity retention rate (%)=retention capacity/initial capacity×100%

Battery capacity recovery rate (%)=recovery capacity/initial capacity×100%

Battery thickness expansion rate (%)=(thickness after 30 days−initial thickness)/initial thickness×100%.

(4) Low-temperature discharge performance test: At 25° C., the formed battery was subjected to 1 C constant current constant voltage charging to 4.35 V, then 1 C constant current discharging to 3.0 V, at which time the discharge capacity was recorded. Then, the battery was subjected to 1 C constant current constant voltage charging to full capacity, allowed to stand in an environment of −20° C. for 12 hours, then subjected to 1 C constant current discharging to 3.0 V, at which time the discharge capacity was recorded.

Low-temperature discharge efficiency value at −20° C.=1 C discharge capacity (−20° C.)/1 C discharge capacity (25° C.).

(5) Normal temperature direct current impedance (DCIR) performance test: Subjecting, at 25° C., the formed battery to 1 C charging to SOC=50%, followed by respectively subjecting the battery to 0.1 C, 0.2 C, 0.5 C, 1 C, and 2 C charging and discharging for 10 seconds and respectively recording the charge and discharge cut-off voltage. Then, a linear relationship plot (unit: mV) was prepared by plotting the charge and discharge currents at different rates on the abscissa (unit: A) and plotting the cut-off voltages corresponding to the charge and discharge currents on the ordinate.

Discharge DCIR value=slope of the linear plot of different discharge currents vs corresponding cut-off voltages.

The test results are shown in Table 2.

1), the cyclic unsaturated carboxylic anhydride compound (CA) preferentially formed a film on the surface of the anode at about 1.5 V and 2 V, and the film preferentially formed by the cyclic unsaturated carboxylic anhydride compound (CA) inhibited the film formation by the unsaturated phosphate (Compound 1) at the subsequent 2.7 V, thereby further lowering the impedance of the anode.

By comparing the test results of Comparative Examples 1-2, it can be found that when the unsaturated phosphate compound was used alone, the cycling performance and the high-temperature storage were good, but the impedance was high and the low-temperature performance was poor. When the unsaturated cyclic carboxylic anhydride compound was used alone, the impedance was low and the low-temperature performance was good, but the cycling performance and the high-temperature storage were poor.

Among the test results of Examples 1-18 of the present application, by comparing Comparative Example 1 with Examples 2, 6, and 8, it can be found that addition of the unsaturated cyclic carboxylic anhydride compound on the basis of the unsaturated phosphate compound not only significantly improved the cycling performance and the high-temperature performance, but also significantly improved the low-temperature performance, and significantly lowered the impedance.

TABLE 2

Test results

| Test item | Cycling capacity retention rate/% 45° C. (1 C/1 C, 300 cycles) | Cycling capacity retention rate/% Normal temperature (1 C/1 C, 500 cycles) | High-temperature storage performance (60° C., 30 days) Capacity retention rate/% | High-temperature storage performance (60° C., 30 days) Capacity recovery rate/% | High-temperature storage performance (60° C., 30 days) Thickness expansion rate/% | 1 C discharge efficiency at −20° C. | 25° C. discharge DCIR/mΩ |
|---|---|---|---|---|---|---|---|
| Comparative Example 1 | 72.1 | 82.8 | 73.5 | 78.9 | 13.5 | 40.3 | 145.6 |
| Comparative Example 2 | 70.2 | 80.1 | 70.3 | 74.6 | 15.5 | 39.3 | 140.2 |
| Example 1 | 75.3 | 83.8 | 77.6 | 80.1 | 10.3 | 42.7 | 129.2 |
| Example 2 | 82.2 | 85.6 | 81.3 | 85.2 | 5.8 | 47.6 | 126.7 |
| Example 3 | 81.9 | 84.6 | 80.1 | 83.4 | 6.8 | 43.5 | 128.9 |
| Example 4 | 81.1 | 83.4 | 80.2 | 83.9 | 7.5 | 42.3 | 131.2 |
| Example 5 | 73.5 | 83.4 | 76.8 | 79.2 | 11.3 | 53.2 | 118.7 |
| Example 6 | 84.3 | 83.6 | 85.3 | 88.3 | 3.8 | 45.3 | 132.7 |
| Example 7 | 85.5 | 83.8 | 85.9 | 88.6 | 5.3 | 43.2 | 135.3 |
| Example 8 | 78.5 | 81.2 | 79.5 | 83.2 | 8.5 | 42.3 | 137.2 |
| Example 9 | 72.5 | 73.5 | 73.5 | 79.2 | 14.8 | 48.7 | 125.3 |
| Example 10 | 80.2 | 81.3 | 78.9 | 84.2 | 8.8 | 45.5 | 125.8 |
| Example 11 | 78.9 | 82.3 | 78.2 | 82.3 | 9.7 | 46.3 | 126.8 |
| Example 12 | 83.3 | 87.5 | 83.2 | 84.5 | 7.8 | 45.6 | 127.8 |
| Example 13 | 80.2 | 82.3 | 80.3 | 83.5 | 5.2 | 47.2 | 125.3 |
| Example 14 | 83.9 | 86.6 | 84.3 | 87.2 | 4.2 | 48.5 | 123.5 |
| Example 15 | 80.1 | 84.6 | 78.3 | 81.3 | 6.8 | 45.5 | 127.2 |
| Example 16 | 83.3 | 82.4 | 82.3 | 85.3 | 4.2 | 44.2 | 129.6 |
| Example 17 | 85.9 | 84.2 | 85.1 | 87.6 | 5.2 | 42.3 | 137.6 |
| Example 18 | 76.5 | 81.9 | 76.5 | 79.2 | 10.5 | 40.3 | 136.2 |

Through the tests, an initial charging capacity differential plot (as shown in FIG. 1) and an AC impedance plot (as shown in FIG. 2) were obtained for the blank electrolyte, Example 6 and Comparative Example 1.

It can be seen from FIG. 1 and FIG. 2 that the unsaturated phosphate (Compound 1) began to form a film on the anode at about 2.7 V during the initial charging process, and the film formation on the anode at this time caused a significant increase in the impedance of the anode. When the cyclic unsaturated carboxylic anhydride compound (CA) was added on the basis of the unsaturated phosphate (Compound Also, among the test results of Examples 1 to 18 of the present application, it can be found that relative to Comparative Example 1, all the Examples containing both the unsaturated phosphate compound and the unsaturated cyclic carboxylic anhydride compound had improved high-temperature performance and low-temperature performance. Comparing Examples 2, 5, 6 and 7, it can be found that as the content of the unsaturated phosphate compound increased, the high-temperature performance improved, but the low-temperature performance was relatively degraded, and especially, as the content increased, the impedance increased accordingly. In particular, when the content of the unsaturated phosphate compound was very high and the content of the unsaturated cyclic carboxylic anhydride compound was very low, the impedance was high and the low-temperature performance was obviously insufficient.

In summary of the above, the present application used the unsaturated phosphate compound and the unsaturated cyclic carboxylic anhydride compound in combination, which, in suitable ratios, allowed the battery to have excellent high-temperature performance and cycling performance as well as good low-temperature performance.

Technical Solution II:

Electrolytes were prepared according to the components and ratios shown in Table 3. A plurality of non-aqueous electrolytes for lithium-ion battery according to the present application as well as a plurality of Comparative Examples were designed, as shown in Table 3 in detail.

The electrolytes in this technical solution were prepared by preparing a non-aqueous organic solvent according to the volume ratio shown in Table 3, and then adding lithium hexafluorophosphate to the solvent to a final concentration of 1.0 mol/L, and then adding the additive according to Table 3. The percentage in Table 3 was percentage by weight, i.e., the percentage of the additive based on the total weight of the electrolyte. The lithium salt content of the electrolyte was 12.5%, and others were solvent grade additives.

TABLE 3

The components and their contents in the electrolytes

| | Total content, composition and weight ratio of the solvent | Additive and its content |
|---|---|---|
| Example 19 | Total content: 87% FEC/PC/EC = 2/1/1 | Tripropargyl phosphate: 0.5% |
| Example 20 | Total content: 86.5% FEC/PC/DEC = 2/1/1 | Tripropargyl phosphate: 1% |
| Example 21 | Total content: 86.5% FEC/PC/EMC = 2/1/1 | Hexafluoroisopropyldipropargyl phosphate: 1% |
| Example 22 | Total content: 86.5% FEC/PC/DEC/EC = 2/1/1/1 | Dipropargyl methyl phosphate: 1% |
| Example 23 | Total content: 86.5% FEC/DFEA = 2/1 | MA: 1% |
| Example 24 | Total content: 86.5% FEC/DFEA/EC = 2/1/1 | CA: 1% |
| Example 25 | Total content: 86.5% FEC/DFEA/DEC = 2/1/1 | Tripropargyl phosphate: 0.5%, CA: 0.5% |
| Example 26 | Total content: 86.5% FEC/PC/DEC = 2/1/1 | Tripropargyl phosphate: 0.5% VC: 0.5% |
| Example 27 | Total content: 86.5% FEC/PC/DEC = 2/1/1 | Tripropargyl phosphate: 0.5% PS: 0.5% |
| Example 28 | Total content: 85.5% FEC/PC/DEC = 2/1/1 | Tripropargyl phosphate: 1% DTD: 1% |
| Example 29 | Total content: 84.5% FEC/PC/DEC = 2/1/1 | Tripropargyl phosphate: 1% DTD: 2% |
| Example 30 | Total content: 85.5% FEC/PC/DEC = 2/1/1 | CA: 1% DTD: 1% |
| Example 31 | Total content: 85% FEC/PC/DEC = 2/1/1 | Tripropargyl phosphate: 1% CA: 0.5 DTD: 1% |
| Example 32 | Total content: 86.5% FEC/DFEA = 2/1 | Tripropargyl phosphate: 0.5% CA: 0.5% |
| Example 33 | Total content: 85.5% FEC/DFEA = 2/1 | Tripropargyl phosphate: 1% DTD: 1% |
| Example 34 | Total content: 85.5% FEC/DFEA = 2/1 | CA: 1% DTD: 1% |
| Example 35 | Total content: 85% FEC/DFEA = 2/1 | Tripropargyl phosphate: 1% CA: 0.5 DTD: 1% |
| Example 36 | Total content: 86.5% FEC/PC/DFEA = 2/1/1 | Tripropargyl phosphate: 0.5% CA: 0.5% |

TABLE 3-continued

The components and their contents in the electrolytes

| | Total content, composition and weight ratio of the solvent | Additive and its content |
|---|---|---|
| Example 37 | Total content: 84.5% FEC/PC/DFEA = 2/1/1 | Tripropargyl phosphate: 1% DTD: 2% |
| Example 38 | Total content: 85.5% FEC/PC/DFEA = 2/1/1 | CA: 1% DTD: 1% |
| Comparative Example 3 | Total content: 87.5% FEC/PC/DEC = 2/1/1 | |
| Comparative Example 4 | Total content: 87.5% FEC/DFEA = 2/1 | |
| Comparative Example 5 | Total content: 87.5% FEC/PC/DFEA = 2/1/1 | |
| Comparative Example 6 | Total content: 87.5% EC/DEC = 2/1 | |
| Comparative Example 7 | Total content: 86.5% EC/DEC = 2/1 | Tripropargyl phosphate: 1% |
| Comparative Example 8 | Total content: 86.5% EC/DEC = 2/1 | CA: 1% |

In the lithium-ion batteries in this technical solution, the cathode active material used was $LiNi_{0.5}Co_{0.2}Mn_{0.3}O_2$, the anode used was artificial graphite and conductive carbon black, and the separator used was a three-layer separator of polypropylene, polyethylene and polypropylene. Specifically, lithium-ion batteries were made as follows.

Preparation of the cathode: Cathode active material $LiNi_{0.5}Co_{0.2}Mn_{0.3}O_2$, conductive carbon black and binder polyvinylidene fluoride were mixed in a mass ratio of 96.8:2.0:1.2. The mixture was dispersed in N-methyl-2-pyrrolidone to obtain a cathode slurry. The cathode slurry was uniformly coated onto both sides of an aluminum foil, which was then subjected to oven drying, calandering and vacuum drying, followed by welding of aluminum lead wires by an ultrasonic welder to obtain the cathode plate, the thickness of the plate being in the range of 120-150 μm.

Preparation of the anode: Graphite, conductive carbon black and binders styrene-butadiene rubber and carboxymethyl cellulose were mixed in a mass ratio of 96:1:1.2:1.8. The mixture was dispersed in deionized water to obtain an anode slurry. The anode slurry was coated onto both sides of a copper foil, which was then subjected to oven drying, calandering and oven drying, followed by welding of nickel lead wires by an ultrasonic welder to obtain the anode plate, the thickness of the plate being in the range of 120-150 μm.

Preparation of the separator: a three-layer separator of polypropylene, polyethylene and polypropylene was used, the thickness being 20 μm.

Battery assembling: the three-layer separator having a thickness of 20 μm was placed between the cathode plate and the anode plate, and the resulting sandwich structure composed of the cathode plate, the anode plate and the separator was wound. The wound structure was flattened and placed into an aluminum foil packing bag, and baked at 85° C. for 24 hours to obtain a battery core, which was to be injected with electrolyte. Then, the battery core was injected with an electrolyte prepared as above, and was vacuum-packed and allowed to stand for 24 hours.

Battery formation: 0.05 C constant current charging for 180 min, 0.1 C constant current charging to 3.95V, vacuum packing again and standing at 45° C. for 48 h, then further, 0.2 C constant current charging to 4.4V, and 0.2 C constant current discharging to 3.0V.

The batteries having the respective electrolytes in this technical solution were subjected to capacity retention rate test of 1 C cycling for 400 cycles at 45° C., and capacity retention rate, capacity recovery rate, and thickness expansion rate tests after storage at 60° C. for 30 days. By "after storage at 60° C. for 30 days" was meant for the electrolytes of the Comparative Examples, the lithium-ion batteries were tested after storage at 60° C. for 30 days, and the Test Examples were tested after storage at 60° C. for 30 days. The specific test methods are as follows:

(1) The capacity retention rate test of 1 C cycling for 400 cycles at 45° C. was in fact to measure the high-temperature cycling performance of the battery. The specific test method comprised: subjecting, at 45° C., the formed battery to 1 C constant current and constant voltage charging to 4.35V, with the cut-off current being 0.01 C, followed by 1 C constant current discharging to 3.0V. This was conducted for 400 cycles. The formula for calculating the capacity retention rate is as follows:

Capacity retention rate (%)=(discharge capacity at the 400$^{th}$ cycle/discharge capacity at the 1$^{st}$ cycle)×100%.

(2) The test method of capacity retention rate, capacity recovery rate and thickness expansion rate after storage at 60° C. for 30 days comprised: subjecting, at a normal temperature, the formed battery to 1 C constant current constant voltage charging to 4.4 V, with the cut-off current being 0.01 C; followed by 1 C constant current discharging to 3.0 V, at which time the initial discharge capacity of the battery was measured, followed by 1 C constant current constant voltage charging to 4.4V, with the cut-off current being 0.01 C, at which time the initial thickness of the battery was measured; followed by storage of the battery at 60° C. for 30 days, at which time the thickness of the battery was measured; followed by 1 C constant current discharging to 3.0V, at which time the retention capacity of the battery was measured; followed by 1 C constant current constant voltage charging, with the cut-off current being 0.01 C; and followed by 1 C constant current discharging to 3.0 V, at which time the recovery capacity was measured. The formulas for calculations are as follows:

Battery capacity retention rate (%)=retention capacity/initial capacity×100%

Battery capacity recovery rate (%)=recovery capacity/initial capacity×100%

Battery thickness expansion rate (%)=(thickness after 30 days−initial thickness)/initial thickness× 100%.

(3) Low-temperature discharge performance test:

At 25° C., the formed battery was subjected to 1 C constant current constant voltage charging to 4.4 V, followed by constant voltage charging until the current decreased to 0.01 C, followed by 1 C constant current discharging to 3.0 V, at which time the normal-temperature discharge capacity was recorded. Then, the battery was subjected to 1 C constant current charging to 4.4 V, followed by constant voltage charging until the current decreased to 0.01 C, followed by allowing the battery to stand in an environment of −20° C. for 12 hours, and followed by 0.2 C constant current discharging to 3.0 V, at which time the discharge capacity at −20° C. was recorded.

Low-temperature discharge efficiency at −20° C.=0.2 C discharge capacity (−20° C.)/1 C discharge capacity (25° C.)×100%

The test results are shown in Table 4.

TABLE 4

| | Test results | | | | |
|---|---|---|---|---|---|
| | | Storage at 60° C. for 30 days | | | 0.2 C |
| | 400 cycles at 45° C. | Capacity retention rate | Capacity recovery rate | Thickness expansion rate | discharge efficiency at −20° C. |
| Example 19 | 80.1% | 83.4% | 88.5% | 17.8% | 72.6% |
| Example 20 | 84.1% | 85.6% | 90.1% | 15.5% | 65.5% |
| Example 21 | 80.5% | 84.6% | 89.1% | 16.5% | 76.5% |
| Example 22 | 79.5% | 81.4% | 86.7% | 19.1% | 76.8% |
| Example 23 | 76.6% | 78.6% | 84.2% | 20.2% | 70.1% |
| Example 24 | 78.6% | 80.2% | 86.1% | 18.2% | 69.4% |
| Example 25 | 82.2% | 84.6% | 88.1% | 16.1% | 70.3% |
| Example 26 | 81.4% | 82.4% | 87.3% | 21.8% | 70.4% |
| Example 27 | 80.5% | 84.6% | 89.3% | 16.2% | 71.2% |
| Example 28 | 85.5% | 85.2% | 91.1% | 14.4% | 74.1% |
| Example 28 | 85.7% | 88.6% | 94.8% | 13.2% | 74.9% |
| Example 30 | 82.1% | 83.4% | 88.7% | 17.4% | 76.2% |
| Example 31 | 87.6% | 88.7% | 94.3% | 10.4% | 73.6% |
| Example 32 | 83.4% | 84.6% | 89.5% | 18.2% | 70.1% |
| Example 33 | 86.4% | 86.5% | 91.8% | 15.6% | 75.1% |
| Example 34 | 83.5% | 84.6% | 89.4% | 18.5% | 75.3% |
| Example 35 | 88.4% | 87.8% | 94.1% | 12.5% | 74.1% |
| Example 36 | 86.5% | 90.7% | 95.4% | 13.2% | 70.3% |
| Example 37 | 88.7% | 89.2% | 94.6% | 13.1% | 75.2% |
| Example 38 | 83.4% | 84.2% | 89.6% | 13.6% | 76.3% |
| Comparative Example 3 | 40% | 44.5% | 50.1% | 53.4% | 76% |
| Comparative Example 4 | 34.3% | 35.2% | 40.5% | 70.4% | 78% |
| Comparative Example 5 | 50.5% | 53.5% | 60.3% | 63.4% | 75% |
| Comparative Example 6 | 30.1% | 60.1% | 68.4% | 40.1% | 70% |
| Comparative Example 7 | 62.1% | 73.4% | 78.6% | 25.3% | 30% |
| Comparative Example 8 | 52.6% | 65.8% | 71.5% | 32.4% | 35% |

It can be seen from the test results in Table 4 that compared with the carbonate solvent, although the fluorinated solvent could improve the high-temperature cycling performance and the low-temperature discharge performance of the battery, the gas production during high-temperature storage was high, which was a safety hazard. Although the unsaturated phosphate and/or the cyclic carboxylic anhydride additive could simultaneously improve the high-temperature cycling performance and the high-temperature storage performance, the extent of improvement was limited and needed to be further increased, and moreover the low-temperature discharge performance was poor. The combination of the fluorinated solvent with the unsaturated phosphate and/or the cyclic carboxylic anhydride could significantly improved the high-temperature storage performance and the high-temperature cycling performance of the battery, without compromising the low-temperature discharge performance. Since there is a certain synergistic effect between the fluorinated solvent and the unsaturated phosphate and/or cyclic carboxylic anhydride, an effect not achievable with the respective single component can be obtained. Further addition of the unsaturated cyclic carbonate or the cyclic sultone or the cyclic sulfate could further improve the high-temperature storage performance and the high-temperature cycling performance of the battery.

Technical Solution III:

In a series of studies on the electrolyte, it was found that the first compound, when used as a non-aqueous organic solvent, decomposes and produces gas at the anode, which poses a safety hazard; and although the second compound can improve the high-temperature performance, it undergoes polymerization reaction on the surface of the cathode and the anode to form a passivation film, which has a high impedance, resulting in reduction in the low-temperature discharge performance and the rate performance of the battery. After extensive research and experimentation, the present applicant proposed that the first compound and the second compound are used in combination to act in synergy, such that the respective advantages and functions of the first compound and the second compound are maintained, and at the same time, the safety hazard of the first compound decomposing at the anode to produce gas is overcome and the influence of the second compound on the low-temperature discharge performance and the rate performance of the battery is alleviated, which greatly improves the performances of the battery.

Electrolytes were prepared according to the components and ratios shown in Table 5, in which a plurality of non-aqueous electrolytes for lithium-ion battery according to the present application and a plurality of comparative examples were designed, as shown in detailed in Table 5.

The respective electrolyte in this technical solution was prepared by preparing a non-aqueous organic solvent in the proportion shown in Table 5, then adding lithium hexafluorophosphate to the solvent to a final concentration of 1.0 mol/L, and then adding the additive according to Table 5. The percentage in Table 5 was percentage by weight, i.e., the percentage of the additive based on the total weight of the electrolyte. The lithium salt content in the electrolyte was 12.5%, the other being solvent-grade additive.

TABLE 5

The components and amounts thereof in the electrolyte

| | Total content, composition and weight ratio of the solvent | Compound of structure formula 4 and amounts thereof | Other additive and amounts thereof |
|---|---|---|---|
| Comparative Example 9 | Content: 86.5% EC/DEC = 1/2 | Tripropargyl phosphate: 1% | — |
| Comparative Example 10 | Content: 87.5% EC/DFEA = 1/2 | — | — |
| Comparative Example 11 | Content: 86.5% EC/DFEA = 1/2 | — | Tris(hexafluoroisopropyl) phosphate: 1% |
| Comparative Example 12 | Content: 86.5% EC/DFEA = 1/2 | — | Tris(trifluoroethyl) phosphate: 1% |
| Comparative Example 13 | Content: 86.5% EC/DFEA = 1/2 | — | Tris(isopropyl)phosphate: 1% |
| Comparative Example 14 | Content: 86.5% FEC/DFEA = 1/2 | — | Tris(hexafluoroisopropyl) phosphate: 1% |
| Comparative Example 15 | Content: 86.5% FEC/DFEA = 1/3 | — | Tris(hexafluoroisopropyl) phosphate: 1% |
| Comparative Example 16 | Content: 86.5% EC/FEC/DFEA = 1/1/2 | — | Tris(hexafluoroisopropyl) phosphate: 1% |
| Comparative Example 17 | Content: 86.5% PC/FEC/DFEA = 1/1/2 | — | Tris(hexafluoroisopropyl) phosphate: 1% |
| Example 39 | Content: 86.5% EC/DFEA = 1/2 | Tripropargyl phosphate: 1% | — |
| Example 40 | Content: 86.5% EC/DFEP = 1/2 | Tripropargyl phosphate: 1% | — |
| Example 41 | Content: 86.5% EC/DFEA = 1/2 | Di(propargyl)ethyl phosphate: 1% | — |
| Example 42 | Content: 86.5% EC/DFEA = 1/2 | Di(propargyl) hexafluoroisopropyl phosphate: 1% | — |
| Example 43 | Content: 86.5% FEC/DFEA = 1/2 | Tripropargyl phosphate: 1% | — |
| Example 44 | Content: 86.5% FEC/DFEA = 1/3 | Tripropargyl phosphate: 1% | — |
| Example 45 | Content: 86.5% EC/FEC/DFEA = 1/1/2 | Tripropargyl phosphate: 1% | — |
| Example 46 | Content: 86.5% PC/FEC/DFEA = 1/1/2 | Tripropargyl phosphate: 1% | — |
| Example 47 | Content: 86.5% PC/FEC/DFEA = 1/1/2 | Di(propargyl)ethyl phosphate: 1% | — |
| Example 48 | Content: 86.5% PC/FEC/DFEA = 1/1/2 | Di(propargyl) hexafluoroisopropyl phosphate: 1% | — |
| Example 49 | Content: 86.5% PC/FEC/DFPA = 1/1/2 | Tripropargyl phosphate: 1% | — |
| Example 50 | Content: 86.5% PC/FEC/DFEP = 1/1/2 | Tripropargyl phosphate: 1% | — |
| Example 51 | Content: 86.5% PC/FEC/DFPP = 1/1/2 | Tripropargyl phosphate: 1% | — |
| Example 52 | Content: 86.5% SL/FEC/DFEA = 1/1/2 | Tripropargyl phosphate: 1% | — |
| Example 53 | Content: 86.5% GBL/FEC/DFEA = 1/1/2 | Tripropargyl phosphate: 1% | — |

TABLE 5-continued

The components and amounts thereof in the electrolyte

| | Total content, composition and weight ratio of the solvent | Compound of structure formula 4 and amounts thereof | Other additive and amounts thereof |
|---|---|---|---|
| Example 54 | Content: 85.5% PC/FEC/DFEA = 1/1/2 | Tripropargyl phosphate: 1% | PS: 1% |
| Example 55 | Content: 85.5% PC/FEC/DFEA = 1/1/2 | Tripropargyl phosphate: 1% | BS: 1% |
| Example 56 | Content: 85.5% PC/FEC/DFEA = 1/1/2 | Tripropargyl phosphate: 1% | PST: 1% |
| Example 57 | Content: 85.5% PC/FEC/DFEA = 1/1/2 | Tripropargyl phosphate: 1% | MMDS: 1% |
| Example 58 | Content: 85.5% PC/FEC/DFEA = 1/1/2 | Tripropargyl phosphate: 1% | DTD: 1% |
| Example 59 | Content: 85.5% PC/FEC/DFEA = 1/1/2 | Tripropargyl phosphate: 1% | CA: 1% |

In the lithium-ion batteries in this technical solution, the cathode active material used was $LiNi_{0.5}Co_{0.2}Mn_{0.3}O_2$, the anode used was graphite and conductive carbon black, and the separator used was a three-layer separator of polypropylene, polyethylene and polypropylene. Specifically, lithium-ion batteries were made as follows.

Preparation of the cathode: Cathode active material $LiNi_{0.5}Co_{0.2}Mn_{0.3}O_2$, conductive carbon black and binder polyvinylidene fluoride were mixed in a mass ratio of 96.8:2.0:1.2. The mixture was dispersed in N-methyl-2-pyrrolidone to obtain a cathode slurry. The cathode slurry was uniformly coated onto both sides of an aluminum foil, which was then subjected to oven drying, calandering and vacuum drying, followed by welding of aluminum lead wires by an ultrasonic welder to obtain the cathode plate, the thickness of the plate being in the range of 120-150 µm.

Preparation of the anode: Graphite, conductive carbon black and binders styrene-butadiene rubber and carboxymethyl cellulose were mixed in a mass ratio of 96:1:1.2:1.8. The mixture was dispersed in deionized water to obtain an anode slurry. The anode slurry was coated onto both sides of a copper foil, which was then subjected to oven drying, calandering and oven drying, followed by welding of nickel lead wires by an ultrasonic welder to obtain the anode plate, the thickness of the plate being in the range of 120-150 µm.

Preparation of the separator: a three-layer separator of polypropylene, polyethylene and polypropylene was used, the thickness being 20 µm.

Battery assembling: the three-layer separator having a thickness of 20 µm was placed between the cathode plate and the anode plate, and the resulting sandwich structure composed of the cathode plate, the anode plate and the separator was wound. The wound structure was flattened and placed into an aluminum foil packing bag, and baked at 75° C. for 48 hours to obtain a battery core, which was to be injected with electrolyte. Then, the battery core was injected with an electrolyte prepared as above, and was vacuum-packed and allowed to stand for 24 hours.

Battery formation: 0.05 C constant current charging for 180 min, 0.1 C constant current charging to 3.95V, vacuum packing again and standing at 45° C. for 48 h, then further, 0.2 C constant current charging to 4.4V, and 0.2 C constant current discharging to 3.0V.

The lithium-ion batteries having the respective electrolytes in this technical solution were subjected to the test for the number of cycles when the capacity retention rate decreased to 80% during 1 C cycling at 45° C., and the tests for the capacity retention rate, capacity recovery rate, and thickness expansion rate after storage at 60° C. for 14 days, wherein storage at 60° C. for a number of days means that the lithium-ion batteries comprising the respective electrolytes in the Comparative Examples were tested after storage at 60° C. for 7 days, and the lithium-ion batteries comprising the respective electrolytes in the Examples were tested after storage at 60° C. for 14 days. The specific test methods are as follows:

The number of cycles when the capacity retention rate decreased to 80% during 1 C cycling at 45° C. in fact represented the high-temperature cycling performance of the battery. The specific test method comprised: subjecting, at 45° C., the formed battery to 1 C constant current and constant voltage charging to 4.4V, with the cut-off current being 0.01 C, followed by 1 C constant current discharging to 3.0V. This cycling was conducted until the capacity retention rate decreased to 80%, at which time the number of cycles was counted. The formula for calculating the capacity retention rate is as follows:

Capacity retention rate (%)=(discharge capacity at the $N^{th}$ cycle/discharge capacity at the $1^{st}$ cycle)×100%.

(2) The test method of capacity retention rate, capacity recovery rate and thickness expansion rate after storage at 60° C. for 14 days comprised: subjecting, at a normal temperature, the formed battery to 1 C constant current constant voltage charging to 4.4 V, with the cut-off current being 0.01 C; followed by 1 C constant current discharging to 3.0 V, at which time the initial discharge capacity of the battery was measured, followed by 1 C constant current constant voltage charging to 4.4V, with the cut-off current being 0.01 C, at which time the initial thickness of the battery was measured; followed by storage of the battery at 60° C. for 14 days, at which time the thickness of the battery was measured; followed by 1 C constant current discharging to 3.0V, at which time the retention capacity of the battery was measured; followed by 1 C constant current constant voltage charging, with the cut-off current being 0.01 C, and followed by 1 C constant current discharging to 3.0V, at which time the recovery capacity was measured. The formulas for calculation are as follows:

Battery capacity retention rate (%)=retention capacity/initial capacity×100%

Battery capacity recovery rate (%)=recovery capacity/initial capacity×100%

Battery thickness expansion rate (%)=(thickness after 14 days−initial thickness)/initial thickness× 100%.

(3) Low-temperature discharge performance test

At 25° C., the formed battery was subjected to 1 C constant current constant voltage charging to 4.4 V, followed by constant voltage charging until the current dropped to 0.01 C, followed by 1 C constant current discharging to 3.0 V, at which time the discharge capacity at normal temperature was recorded. Then, the battery was subjected to 1 C constant current charging to 4.4V, followed by constant voltage charging until the current dropped to 0.01 C, followed by allowing the battery to stand in an environment of −20° C. for 12 hours, followed by 0.2 C constant current discharging to 3.0 V, at which time the discharge capacity at −20° C. was recorded.

Low-temperature discharge efficiency at −20° C.=0.2 C discharge capacity (−20° C.)/1 C discharge capacity (25° C.)×100%.

The test results are shown in Table 6.

TABLE 6

| | Test results | | | | |
|---|---|---|---|---|---|
| | Number of cycles when the capacity retention rate decreased to 80% during 1 C cycling at 45° C. | Storage at 60° C. for 14 days | | | 0.2 C discharge efficiency at −20° C. |
| | | Capacity retention rate | Capacity recovery rate | Thickness expansion rate | |
| Comparative Example 9 | 290 | 47% | 51% | 15% | 40% |
| Comparative Example 10 | 250 | 20.1% | 25.3% | 42% | 77.5% |
| Comparative Example 11 | 365 | 78.2% | 82.3% | 20.6% | 73.4% |
| Comparative Example 12 | 354 | 76.4% | 80.7% | 24.5% | 72.5% |
| Comparative Example 13 | 330 | 74.4% | 78.6% | 28.4% | 73.2% |
| Comparative Example 14 | 400 | 80.5% | 84.5% | 32.4% | 74.1% |
| Comparative Example 15 | 387 | 79.5% | 84.1% | 27% | 73.2% |
| Comparative Example 16 | 390 | 80.1% | 84.7% | 26.4% | 71.3% |
| Comparative Example 17 | 420 | 82.1% | 87.2% | 26.5% | 74.5% |
| Example 39 | 430 | 83.5% | 87.5% | 12.4% | 68.1% |
| Example 40 | 445 | 84.5% | 88.4% | 11.8% | 69.4% |
| Example 41 | 425 | 81.2% | 85.1% | 14.4% | 72.5% |
| Example 42 | 420 | 79.1% | 84.6% | 16.5% | 73.9% |
| Example 43 | 510 | 85.2% | 89.3% | 18.2% | 70.5% |
| Example 44 | 505 | 84.6% | 89.1% | 15.7% | 72.1% |
| Example 45 | 526 | 86.7% | 90.5% | 15.5% | 71.6% |
| Example 46 | 574 | 88.1% | 92.2% | 13.5% | 73.4% |
| Example 47 | 554 | 86.3% | 90.7% | 14.8% | 74.5% |
| Example 48 | 535 | 84.4% | 88.4% | 16.6% | 75.1% |
| Example 49 | 589 | 88.9% | 92.6% | 12.5% | 73.6% |
| Example 50 | 612 | 90.1% | 94.2% | 12.1% | 74.6% |
| Example 51 | 631 | 91.1% | 95.2% | 11.5% | 75.1% |
| Example 52 | 512 | 83.1% | 87.5% | 20.5% | 65.3% |
| Example 53 | 522 | 84.4% | 88.5% | 17.5% | 64.2% |
| Example 54 | 590 | 89.5% | 93.5% | 12.1% | 70.4% |
| Example 55 | 595 | 89.2% | 93.7% | 13.3% | 70.8% |
| Example 56 | 620 | 90.5% | 94.9% | 12.4% | 68.5% |
| Example 57 | 650 | 90.9% | 95.2% | 12.3% | 74.1% |
| Example 58 | 655 | 90.5% | 94.5% | 13.6% | 76.2% |
| Example 59 | 662 | 89.4% | 92.1% | 11.1% | 69.6% |

According to the results in Table 6, it can be seen that in Comparative Example 9 that only used the second compound as an additive and did not use the first compound as a solvent, the high-temperature cycling performance was weak, the capacity retention rate left was 80% after 290 cycles, and the storage capacity and recovery capacity after storage at 60° C. for 14 days were not satisfactory either, especially the low-temperature discharge performance was relatively poor. In Comparative Example 10 that used the first compound as a solvent and did not use the second compound as an additive, the high-temperature storage performance and the high-temperature storage performance were both very poor. In Comparative Example 11-17 that used the first compound as a solvent, used saturated phosphate as an additive, and also optimized the solvent combination, although the high-temperature cycling performance and the high-temperature storage performance of the batteries were greatly improved, the batteries still failed to meet the requirements, needed to be further improved. In Examples 39-59 that used the first compound as a solvent and the second compound as an additive and also optimized the solvent combination and the additive combination, the high-temperature cycling performance and the high-temperature storage performance were both markedly improved, without compromising the low-temperature discharge performance. In Example 59, the high-temperature cycling performance was the best, reduction of the capacity retention rate to 80% only resulted after 662 cycles, and the high-temperature storage performance was also excellent.

The above is a further detailed description of the present application in conjunction with particular embodiments, and the specific implementation of the present application is not to be construed as limiting to such description. It will be apparent to those skilled in the art that several simple derivations and substitutions can be made without departing from the concept of the present application and such derivations and substitutions shall be deemed to fall within the scope of protection of the present application.

The invention claimed is:

1. A non-aqueous electrolyte for lithium-ion battery, comprising Component B, wherein Component B comprises an unsaturated phosphate compound and a cyclic unsaturated carboxylic anhydride compound, the unsaturated phosphate compound having a structure represented by Structural Formula 4, Structural Formula 4 wherein $R_{13}$, $R_{11}$ and $R_{12}$ are each independently selected from a hydrocarbon group having 1 to 5 carbon atoms, and at least one of $R_{13}$, $R_{11}$ and $R_{12}$ is an unsaturated hydrocarbon group having a double bond or a triple bond; and the unsaturated cyclic carboxylic anhydride compound having a structure represented by Structural Formula 5,

Structural Formula 5 wherein $R_{14}$ is selected from the group consisting of an alkenylene group having 2 to 4 carbon atoms or a fluorinated alkenylene group having 2 to 4 carbon atoms.

2. The non-aqueous electrolyte according to claim 1, wherein the hydrocarbon group having 1 to 5 carbon atoms of the unsaturated phosphate compound is selected from the group consisting of methyl, ethyl, propyl, vinyl, allyl, 3-butenyl, isobutenyl, ethynyl, propargyl, 3-butynyl, and 1-methyl-2-propynyl group.

3. The non-aqueous electrolyte according to claim 1, wherein the unsaturated phosphate compound is one or more selected from the group consisting of tripropargyl phosphate, dipropargyl methyl phosphate, dipropargylethyl phosphate, dipropargylpropyl phosphate, triallyl phosphate, diallyl methyl phosphate, diallyl ethyl phosphate, diallyl propyl phosphate, and propargyl dipropyl phosphate.

4. The non-aqueous electrolyte according to claim 3, wherein the unsaturated phosphate compound is one or more selected from the group consisting of:

5. The non-aqueous electrolyte according to claim 1, wherein the cyclic unsaturated carboxylic anhydride is one or more selected from the group consisting of maleic anhydride, 2-methylmaleic anhydride, succinic anhydride, and glutaric anhydride.

6. The non-aqueous electrolyte according to claim 5, wherein the cyclic unsaturated carboxylic anhydride is one or more selected from the group consisting of maleic anhydride and 2-methylmaleic anhydride.

7. The non-aqueous electrolyte according to claim 1, wherein in the non-aqueous electrolyte, the unsaturated phosphate compound accounts for 0.1% to 3% of the total weight of the non-aqueous electrolyte for lithium-ion battery, and the cyclic unsaturated carboxylic anhydride compound accounts for 0.1% to 3% of the total weight of the non-aqueous electrolyte for lithium-ion battery.

8. The non-aqueous electrolyte according to claim 1, wherein the non-aqueous electrolyte further comprises at least one selected from the group consisting of an unsaturated cyclic carbonate, a cyclic sultone, and a cyclic sulfate.

9. The non-aqueous electrolyte according to claim 8, the unsaturated cyclic carbonate compound accounts for 0.1% to 5% of the total weight of the non-aqueous electrolyte, or the cyclic sultone compound accounts for 0.1% to 5% of the total weight of the non-aqueous electrolyte, or the cyclic sulfate compound accounts for 0.1% to 5% of the total weight of the non-aqueous electrolyte.

10. The non-aqueous electrolyte according to claim 8, wherein the unsaturated cyclic carbonate is at least one selected from the group consisting of vinylene carbonate and vinylethylene carbonate.

11. The non-aqueous electrolyte according to claim 8, the cyclic sultone is at least one selected from the group consisting of 1,3-propane sultone, 1,4-butane sultone, 1,3-propene sultone and methylene methanedisulfonate.

12. The non-aqueous electrolyte according to claim 8, the cyclic sulfate is one or both selected from the group consisting of vinyl sulfate and propylene sulfate.

13. The non-aqueous electrolyte according to claim 1, wherein the non-aqueous electrolyte comprises a non-aqueous organic solvent and a lithium salt.

14. The non-aqueous electrolyte according to claim 13, wherein the non-aqueous organic solvent being at least one selected from the group consisting of ethylene carbonate, propylene carbonate, butylene carbonate, dimethyl carbonate, diethyl carbonate, methyl ethyl carbonate, and methyl propyl carbonate.

15. The non-aqueous electrolyte according to claim 13, wherein and the lithium salt being at least one selected from the group consisting of lithium hexafluorophosphate, lithium tetrafluoroborate, lithium bis (trifluoromethanesulfonyl)imide, and lithium difluorosulfonimide.

16. A lithium-ion battery, comprising a cathode, an anode, a separator interposed between the cathode and the anode, and an electrolyte, wherein the electrolyte is the non-aqueous electrolyte according to claim 1.

17. The lithium-ion battery according to claim 16, wherein the cathode comprises a cathode active material, the cathode active material being at least one selected from the group consisting of $LiCoO_2$, $LiNiO_2$, $LiMn_2O_4$, $LiCo_{1-y}M_yO_2$, $LiNi_{1-y}M_yO_2$, $LiMn_{2-y}M_yO_4$ and $LiNi_xCo_yMn_zM_{1-x-y-z}O_2$; wherein M is at least one selected from the group consisting of Fe, Co, Ni, Mn, Mg, Cu, Zn, Al, Sn, B, Ga, Cr, Sr, V, and Ti, and $0 \leq y \leq 1$, $0 \leq x \leq 1$, $0 \leq z \leq 1$, and $x+y+z \leq 1$.

18. The lithium-ion battery according to claim 16, wherein the cathode comprises a cathode active material, the cathode active material being at least one selected from the group consisting of $LiNi_xCo_yMn_zL_{(1-x-y-z)}O_2$, $LiCo_xL_{(1-x')}O_2$ and $LiNi_{x'}L'_{y'}Mn_{(2-x''-y')}O_4$, wherein L is Al, Sr, Mg, Ti, Ca, Zr, Zn, Si or Fe, $0 \le x \le 1$, $0 \le y \le 1$, $0 \le z \le 1$, $0 < x+y+z \le 1$, $0 < x' \le 1$, $0.3 \le x'' \le 0.6$, and $0.01 \le y' \le 0.2$, and L' is Co, Al, Sr, Mg, Ti, Ca, Zr, Zn, Si or Fe.

19. The lithium-ion battery according to claim 16, wherein the lithium-ion battery has a charge cut-off voltage of greater than or equal to 4.3V.

* * * * *